United States Patent
Carbonelli et al.

(10) Patent No.: US 11,193,881 B2
(45) Date of Patent: Dec. 7, 2021

(54) GAS SENSING DEVICE FOR SENSING A GAS IN A MIXTURE OF GASES AND METHOD FOR OPERATING A GAS SENSING DEVICE

(71) Applicant: Infineon Technologies AG, Neubiberg (DE)

(72) Inventors: Cecilia Carbonelli, Munich (DE); Alessandra Fusco, Munich (DE); Johannes Manz, Munich (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 0 days.

(21) Appl. No.: 16/919,828

(22) Filed: Jul. 2, 2020

(65) Prior Publication Data

US 2021/0025811 A1 Jan. 28, 2021

(30) Foreign Application Priority Data

Jul. 26, 2019 (EP) .................................... 19188601

(51) Int. Cl.
*G01N 21/17* (2006.01)

(52) U.S. Cl.
CPC . *G01N 21/1702* (2013.01); *G01N 2021/1704* (2013.01)

(58) Field of Classification Search
CPC ....... G01N 21/1702; G01N 2021/1704; G01N 29/02; G01N 29/2425; G01N 29/46; G01N 2291/0215
See application file for complete search history.

(56) References Cited

U.S. PATENT DOCUMENTS

| | | | | |
|---|---|---|---|---|
| 6,529,276 B1* | 3/2003 | Myrick | ...................... | G01J 3/02 356/419 |
| 2004/0122709 A1* | 6/2004 | Avinash | ................. | G16H 40/67 705/2 |
| 2012/0266653 A1* | 10/2012 | Yaniv | ................. | A61B 5/14551 73/23.3 |
| 2017/0038257 A1* | 2/2017 | Liu | ...................... | G01N 21/274 |

FOREIGN PATENT DOCUMENTS

| | | |
|---|---|---|
| CN | 104614337 A | 5/2015 |
| DE | 102012217479 B3 | 10/2013 |
| WO | 2007067922 A2 | 6/2007 |

\* cited by examiner

*Primary Examiner* — Suman K Nath

(74) *Attorney, Agent, or Firm* — Slater Matsil, LLP

(57) ABSTRACT

A gas sensing device includes a photoacoustic spectrometry device, including a radiator for emitting light, a gas detection chamber for exposing a mixture of gases to the light, a microphone for detecting sound in the detection chamber, which is caused by exposing the mixture of gases to the light, and wherein the photoacoustic spectrometry device generates signal samples corresponding to a concentration of the gas in the mixture of gases based on the sound detected by the microphone, and a computing device for receiving the signal samples. The computing device includes a feature extraction block including a trained model algorithm block.

13 Claims, 13 Drawing Sheets

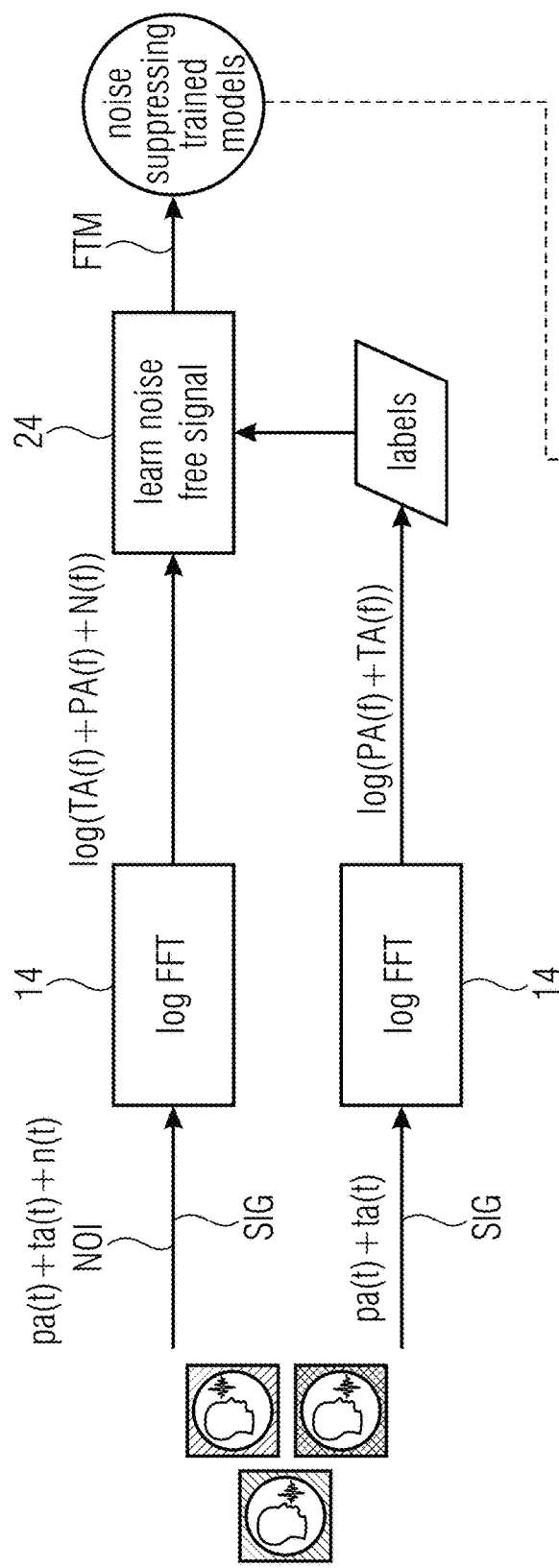
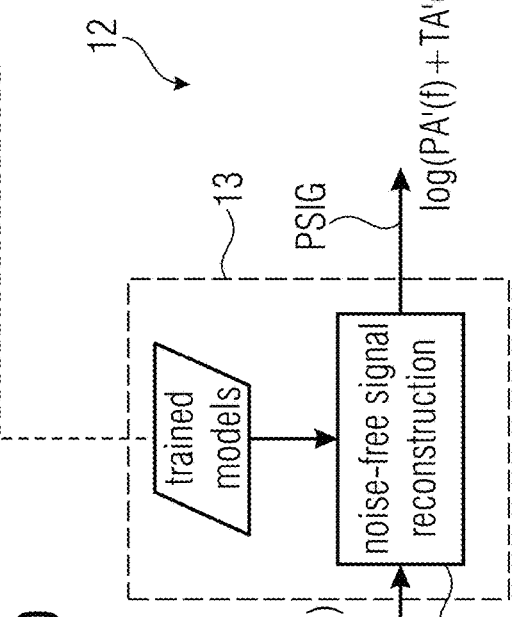
Fig. 10
Fig. 11

GAS SENSING DEVICE FOR SENSING A GAS IN A MIXTURE OF GASES AND METHOD FOR OPERATING A GAS SENSING DEVICE

This application claims the benefit of European Patent Application No. 19188601, filed on Jul. 26, 2019, which application is hereby incorporated herein by reference.

TECHNICAL FIELD

Embodiments relate to a gas sensing device for sensing a gas in a mixture of gases. Further embodiments relate to a method for operating such gas sensing device. More particular, the disclosure deals with the estimation of gas concentrations through the use of photoacoustic spectrometry devices.

BACKGROUND

Several types of gas sensors with different operation mechanisms (e.g. MOS, infrared, electrochemical, etc.), different form factors (portable or fixed devices) and different target applications (medical, industrial, automotive, mobile phones, etc.) are known in the art.

Acoustic coupling represents a problem for those sensors which make use of a microphone to detect pressure changes which are proportional to the amount of gas concentration present in the measurement volume. This is the case of so-called "open" non-resonant photoacoustic gas sensors, where the microphone is placed in the measurement volume and the system operates at a relatively low frequency (<100 Hz).

So-called "closed" photoacoustic sensors experience less significant degradations due to acoustic noise, since the microphone is hermetically closed in the detector case and thus at least partially isolated from the outside noisy environment. Similarly, resonant open photo acoustic gas sensors, which operate at very high frequency and have very narrow spectrum, are less prone to degradations due to acoustic noise. However, closed photoacoustic sensors and resonant open photo acoustic gas sensors are bulky, cost intensive and not suitable for high end applications where a high level of sensitivity, a wide measurement range and a fast time response is required.

SUMMARY

A gas sensing device for sensing a gas in a mixture of gases is provided. The gas sensing device comprises:

a photoacoustic spectrometry device, wherein the photoacoustic spectrometry device comprises a radiator configured for emitting light, wherein the photoacoustic spectrometry device comprises a gas detection chamber configured for exposing the mixture of gases to the light, wherein the photoacoustic spectrometry device comprises a microphone configured for detecting sound in the detection chamber, which is caused by exposing the mixture of gases to the light, and wherein the photoacoustic spectrometry device is configured for generating signal samples corresponding to a concentration of the gas in the mixture of gases based on the sound detected by the microphone; and a computing device configured for receiving the signal samples, wherein the computing device comprises a feature extraction block configured for calculating representations for the signal samples so that for each of the signal samples one of the representations is calculated, wherein each of the representations comprises one or more feature values, wherein each of the one or more feature values refer to a characteristic of the respective signal sample, wherein the computing device comprises a decision making block which comprises a trained model based algorithm block having a plurality of inputs and at least one output, wherein the decision making block comprises one or more trained models for the trained model based algorithm block, wherein each of the feature values of one of the representations is input to one of the inputs of the trained model based algorithm block, so that each feature value of the feature values is fed into an individual input of the inputs, wherein the decision making block creates sensing results based on output values of the at least one output of the trained model based algorithm block, wherein the output values are created by using at least one of the one or more trained models at the decision making block so that the output values depend on the signal samples of the photoacoustic spectrometry device.

The photoacoustic spectrometry device is configured for measuring the effect of absorbed electromagnetic energy, particularly of light on matter by acoustic detection. It may be used for measuring accurately the concentrations of various gases due to its ability to evaluate subject samples in its in-situ state. The photoacoustic spectrometry device may be of the open type or of the closed type. It may be resonant photoacoustic spectrometry device or a non-resonant photoacoustic spectrometry device.

The radiator in general may be configured for emitting light of a specific wavelength which can only be absorbed by a specific gas, so that the specific gas may be detected. The radiator may comprise a laser or any other light source. Further, the radiator may comprise optical filters in order to filter the produced light in such way that the wavelength of the emitted light corresponds to the desired specific wavelength. The specific wavelength may be in the range of visible light or in the range of infrared light. The emitted light may be coherent or non-coherent.

A signal sample is a sequence consisting of time-discrete signal values, wherein the signal values are output by one of the gas sensors.

The feature extraction block may be configured for transforming the signal samples into representations, wherein the representations are based on characteristics of the signal samples. Some of the feature values of the representations may correspond to the absolute value of the mean deviation of the respective signal sample, to the phase of the mean deviation of the respective signal sample, to the absolute value of the standard deviation of the respective signal sample or to the phase of the standard deviation of the respective signal sample.

The decision making block receives the representations during operational phases, wherein the decision making block comprises a trained model based algorithm block and one or more trained models for the trained model based algorithm block.

The trained model based algorithm block is a processing stage which is capable of machine learning. The machine learning is done in a preoperational training phase in which trained models are developed by comparing actual output values of the trained model based algorithm block with desired output values of the trained model based algorithm block for defined inputs of the trained model based algorithm stage. The trained models have a predefined structure, wherein a parametrization of the predefined structure is done during the training phase. The trained models comprise the learned content after the training phase is finished. In an operational phase for producing sensing results one or more of the trained models from the training phase are used to process the representations from the feature extraction block.

In the training phase the plurality of trained models can be established and afterwards stored at the decision making block. The trained models may differ in the structures and/or the parameters. During an operation phase the most appropriate trained model may be selected depending on the specific use-case.

The trained model based algorithm block comprises a plurality of inputs and at least one output, wherein each of the feature values of one of the representations is input to one of the inputs of the trained model based algorithm block, so that each feature value of the feature values is fed into an individual input of the inputs, wherein the decision making block creates sensing results based on output values of the at least one output of the trained model based algorithm block, wherein the output values are created by using at least one of the one or more trained models at the decision making block so that the output values depend on the signal samples of the photoacoustic spectrometry device.

The decision making block provides a decision on the classification of gas concentrations detected by the photoacoustic spectrometry device or a continuous measurement of gas concentrations detected by the photoacoustic spectrometry device. In the first case a trained model, which is trained as a classification algorithm, is used and the sensing results are alphanumeric terms such as "high" or "low". In the latter case a trained model, which is trained as a regression algorithm, is used and the sensing results are physical quantities such as "4% by volume".

The gas sensing device according to the disclosure addresses the intrinsic susceptibility to acoustic noise of photoacoustic spectrometry devices. It uses robust algorithms and detection mechanisms which can cope with calibration inaccuracies, drifts and other similar effects reliably and over a wide operating range.

The proposed gas sensing device provides an end to end solution for gas sensors based on photoacoustic spectrometry devices, which is versatile, widely-applicable to multiple applications and uses cases (outdoor, indoor, health check, etc.) and can be embedded in a smart portable device. In particular, the gas sensing device may be used for air quality monitoring. Specifically, an algorithm is used that works on continuous sensor readings, makes use of the features in the sensor responses and exhibits low complexity and limited memory requirements.

The gas sensing device can reflect real world scenarios, where, for example, gas mixtures are present which are causing cross-sensitivities in the sensor responses. Moreover, the gas sensing device only takes a short time for reaching a stable response level.

The material costs of the gas sensing device are low and it uses concrete mechanisms which are robust and economic enough to be embedded into mass-produced consumer electronic products (like a mobile phone), while delivering good continuous prediction performance in complicated real world scenarios, and as such have to deal with challenges related to the availability of a limited and noisy sets of data, imperfect initial calibration, gas mixtures with varying concentrations of analytes, modelling errors, etc.

Relying on a nonlinear activation function, the gas sensing device according to the disclosure overcomes the limitations of the state of the art sensors relying on linear regression fit methods. The proposed methodology is able to model nonlinear dependencies between the measure metrics and the parameter to estimate. As a result, the sensor performance is remarkably improved.

The gas sensing device according to the disclosure is suitable for a wide range of applications including high end applications where a high level of accuracy, a high level of sensitivity, a wide measurement range and a fast time response is required.

According to embodiments of the disclosure the computing device comprises a preprocessing block, wherein the preprocessing block is configured for receiving the signal samples from the photoacoustic spectrometry device, wherein the preprocessing block is configured for generating a preprocessed signal sample for each of the signal samples, and wherein the preprocessing block is configured for forwarding the preprocessed signal samples to the feature extraction block.

In such embodiments the feature extraction block may calculate the representations for the signal samples by processing the preprocessed signal samples.

According to embodiments of the disclosure the preprocessing block comprises a noise suppression block configured for suppressing noise, in particular noise caused by ambient acoustic noise, in the signal samples, so that the preprocessed signal samples comprise noise reduced signal samples having less noise than the corresponding signal sample.

By such features the performance of the gas sensing device may be further improved.

According to embodiments of the disclosure the trained model based algorithm block comprises a neural network using the one or more trained models and/or a random decision forest using the one or more trained models.

A random decision forest is a learning method for classification, regression and other tasks that operates by constructing a multitude of decision trees at training time and outputting the class that is the mode of the classes (classification) or mean prediction (regression) of the individual trees.

An artificial neural network is a parameterized statistic model, in which a number of logistic regressions are combined non-linearly. Such systems "learn" to perform tasks by considering examples, generally without being programmed with any task-specific rules. A neural network is based on a collection of connected nodes called artificial neurons. Each connection can transmit a signal from one artificial neuron to another. An artificial neuron that receives a signal can process it and then signal additional artificial neurons connected to it. The structure of the nodes, or the hyperparameters, of a neural network is predefined by a model and the parameters of the connections are found by training the neural network. Structure and the corresponding parameters form a trained model for the respective neural network.

The neural network may be, for example, a fully connected feedforward neural network with one hidden layer.

According to embodiments of the disclosure the preprocessing block comprises a domain transform block configured for transforming the signal samples into a log-frequency domain, so as to obtain a logarithmic spectrum having a plurality of frequency bands for each of the signal samples, wherein the noise suppression block comprises a further trained model based algorithm block having a plurality of inputs and a plurality of outputs, wherein the noise suppression block comprises one or more further trained models for the further trained model based algorithm block, wherein for each frequency band of the logarithmic spectra of one of the signal samples an amplitude value and a phase value are input to one of the inputs of the further algorithm block, so that each of the amplitude values and each of the phase values are fed into an individual input of the inputs, wherein the noise suppression block creates the noise reduced signal samples based on output values of the outputs of the further trained model based algorithm block, wherein the output values of the further trained model based algorithm block are created by using at least one of the one or more further trained models at the noise suppression block, and wherein each of the output values of the further trained model based algorithm block is a noise reduced amplitude value or a noise reduced phase value of a noise reduced frequency band of a noise reduced logarithmic spectra of one of the preprocessed signal samples.

The transformation of the signal samples from a time domain into a log-frequency domain leads to a reduction of the amount of data which has to be processed in the following processing blocks. In particular, it simplifies the handling of noises this difference spectral properties.

The general remarks regarding the trained models and the trained model based algorithm block of the decision making block are valid also for the further trained models and the further trained model based algorithm block of a noise suppression block. However, the trained models and the further trained models have to be established separately. In the latter case, during the training phase the microphone output is used with and without acoustic noise. The further trained model based algorithm block may be implemented as a de-noising auto-encoder. In particular, such embodiments of the noise suppression block are most suitable in case the photoacoustic spectrometry device is of the closed type, as closed type photoacoustic spectrometry devices in general comprise a mechanism for letting the mixture of gas into and out of the sensing chamber, which may produce acoustic noise.

According to embodiments of the disclosure the further trained model based algorithm block comprises a further neural network using the one or more further trained models and/or a further random decision forest using the one or more further trained models.

The further neural network may be, for example, a fully connected feedforward neural network with one hidden layer.

According to embodiments of the disclosure the preprocessing block comprises a domain transform block configured for calculating a logarithmic spectrum having a plurality of frequency bands for each of the signal samples.

The transformation of the signal samples from a time domain into a log-frequency domain leads to a reduction of the amount of data which has to be processed in the following processing blocks also in such cases in which the decision making block does not comprise a further trained model based algorithm block.

According to embodiments of the disclosure the noise suppression block comprises a band-pass filter or a low-pass filter, so that the preprocessed signal samples are based on bandwidth reduced signal samples having a lower bandwidth than the corresponding signal sample.

A band-pass filter is a filter that passes frequencies within a certain frequency range and attenuates frequencies outside that frequency range. A low-pass filter is a filter that passes signals with a frequency lower than a selected cutoff frequency and attenuates signals with frequencies higher than the cutoff frequency.

The use of the frequency filter is preferred in such cases in which access to the microphone output without noise isn't possible or if separate training phases for the trained models and the further trained models and the desired for complexity reasons.

According to embodiments of the disclosure the gas sensing device comprises one or more auxiliary sensors, wherein each of the auxiliary sensors is configured for generating auxiliary signal samples corresponding to a physical quantity of the mixture of gases;

wherein the one or more auxiliary sensors comprise a temperature sensor for generating first auxiliary signal samples of the auxiliary signal samples, which correspond to a temperature of the mixture of gases, and/or a pressure sensor for generating second auxiliary signal samples of the auxiliary signal samples, which correspond to a pressure of the mixture of gases, and/or a humidity sensor for generating third auxiliary signal samples of the auxiliary signal samples, which correspond to a humidity of the mixture of gases.

By these features the accuracy of the gas sensing device may be further increased.

According to embodiments of the disclosure the decision making block is configured for selecting one or more selected trained models from the one or more trained models based on the auxiliary signal samples of the one or more auxiliary sensors, wherein the output values of the at least one output of the algorithm are created by using the one or more selected trained models.

For example the most appropriate trained model could be chosen based on the humidity value obtained from a humidity sensor as humidity has an impact on the sensor responses.

By these features the accuracy of the gas sensing device may be further increased.

According to embodiments of the disclosure the decision making block is configured for selecting the one or more selected trained models based on spectral information of the signal samples.

Spectral portions of the signal samples, e.g. very low frequencies, may correlate to environmental parameters of the mixture of gases, such as pressure, temperature or humidity. Thus, such features may replace measurement data from auxiliary sensors, so that the need of having auxiliary sensors measuring such environmental parameters may be eliminated.

According to embodiments of the disclosure the feature extraction block is configured for calculating auxiliary representations for the auxiliary signal samples so that for each of the auxiliary signal samples one of the auxiliary representations is calculated, wherein each of the auxiliary representations comprises one or more auxiliary feature values, wherein each of the one or more auxiliary feature values refer to a characteristic of the respective auxiliary signal sample; and wherein each of the auxiliary feature values of one of the auxiliary representations is input to one of the inputs of the trained model based algorithm block, which is not used for inputting feature values, so that each of the auxiliary feature values is fed into an individual input of the inputs, wherein the output values of the trained model based algorithm block are created so that the output values depend on the auxiliary signal samples.

Some of the auxiliary feature values of the representations may correspond to the absolute value of the mean deviation of the respective auxiliary signal sample, to the phase of the mean deviation of the respective auxiliary signal sample, to the absolute value of the standard deviation of the respective auxiliary signal sample or to the phase of the standard deviation of the respective auxiliary signal sample.

By these features the accuracy of the gas sensing device may be further increased.

According to embodiments of the disclosure the detection chamber comprises one or more ventilation openings which are permanently open during an operational phase of the gas sensing device.

Permanently open ventilation openings allow permanent exchange between the mixture of gases within the detection chamber and an ambient mixture of gases so that a change of the concentration of the gas to be detected in the ambient mixture of gases can be detected without delay. A photoacoustic spectrometry device having such ventilation openings may also be referred to as an open type photoacoustic spectrometry device.

A further aspect of the disclosure relates to a method for operating a gas sensing device for sensing a gas in a mixture of gases, wherein the gas sensing device comprises a photoacoustic spectrometry device, wherein the photoacoustic spectrometry device comprises a radiator configured for emitting light, wherein the photoacoustic spectrometry device comprises a gas detection chamber configured for exposing the mixture of gases to the light, and wherein the photoacoustic spectrometry device comprises a microphone configured for detecting sound in the detection chamber, which is caused by exposing the mixture of gases to the light, and wherein the gas sensing device comprises a computing device comprising a feature extraction block and a decision making block, wherein the decision making block comprises a trained model based algorithm block having a plurality of inputs and at least one output, wherein the decision making block comprises one or more trained models for the trained model based algorithm block, wherein the method comprises the steps of:

using the photoacoustic spectrometry device for generating signal samples corresponding to a concentration of the gas in the mixture of gases based on the sound detected by the microphone;

using a computing device for receiving the signal samples, wherein the computing device comprises a feature extraction block and a decision making block, wherein the decision making block which comprises a trained model based algorithm block having a plurality of inputs and at least one output, wherein the decision making block comprises one or more trained models for the algorithm block;

using the feature extraction block for calculating representations for the signal samples so that for each of the signal samples one of the representations is calculated, wherein each of the representations comprises one or more feature values, wherein each of the one or more feature values refer to a characteristic of the respective signal sample;

inputting each of the feature values of one of the representations to one of the inputs of the trained model based algorithm block, so that each feature value of the feature values is fed into an individual input of the inputs; and using the decision making block for creating sensing results based on output values of the at least one output of the trained model based algorithm block, wherein the output values are created by using at least one of the one or more trained models at the decision making block so that the output values depend on the signal samples of the photoacoustic spectrometry device.

BRIEF DESCRIPTION OF THE DRAWINGS

Embodiments of the present invention are described herein making reference to the appended drawings.

FIG. 10 illustrates a general approach of training a further trained model for a further trained model based algorithm block for a noise suppression block for a gas sensing device according to the disclosure;

FIG. 11 illustrates a general approach of operating a first preprocessing block for a gas sensing device according to the disclosure;

Figure 1:
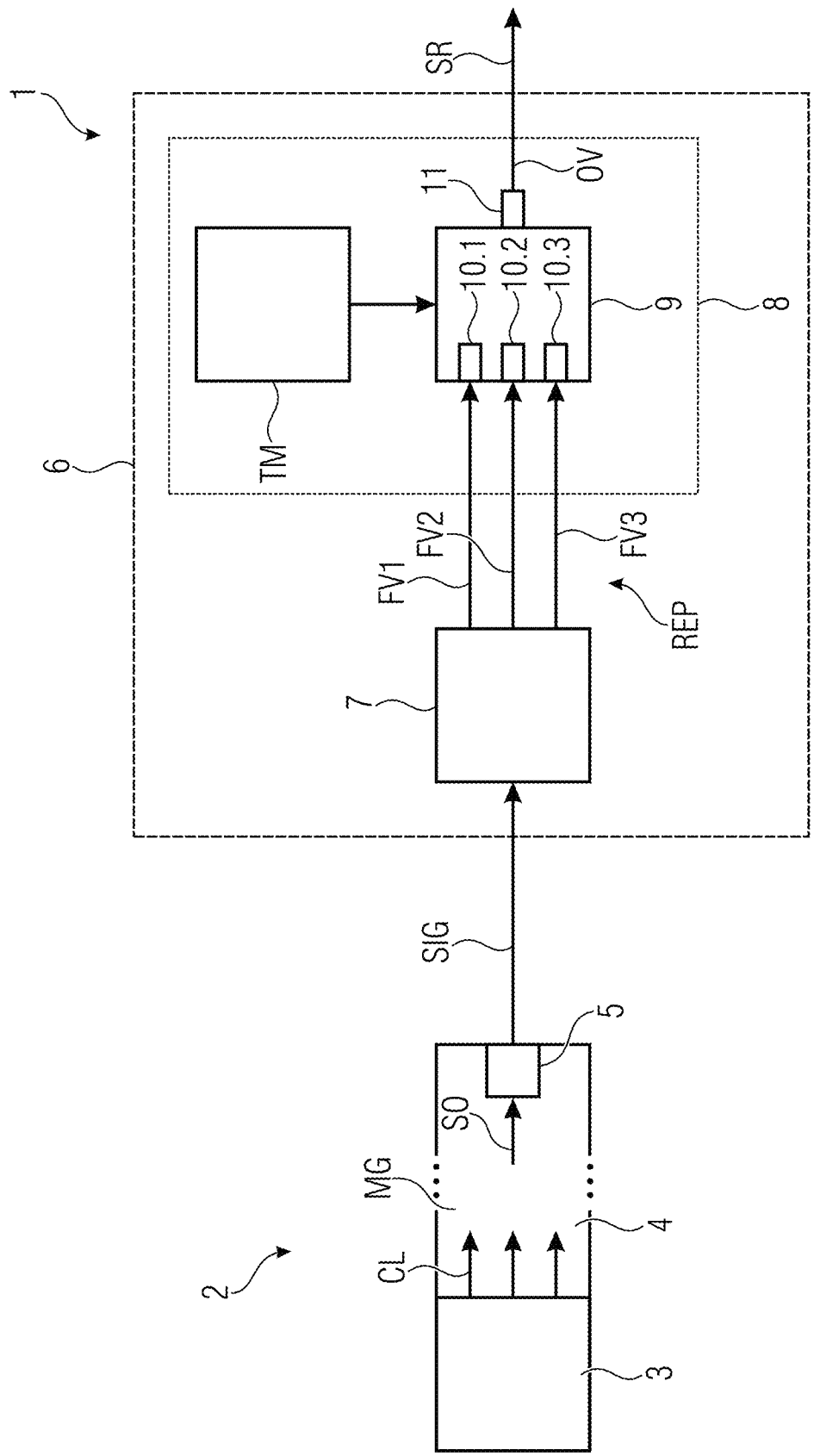
FIG. 1 shows a schematic view of a first embodiment of a gas sensing device according to the disclosure.

Equal or equivalent elements or elements with equal or equivalent functionality are denoted in the following description by equal or equivalent reference numerals.

DETAILED DESCRIPTION OF ILLUSTRATIVE EMBODIMENTS

In the following description, a plurality of details is set forth to provide a more thorough explanation of embodiments of the present invention. However, it will be apparent to those skilled in the art that embodiments of the present invention may be practiced without these specific details. In other instances, well-known structures and devices are shown in block diagram form rather than in detail in order to avoid obscuring embodiments of the present invention. In addition, features of the different embodiments described hereinafter may be combined with each other, unless specifically noted otherwise.

FIG. 1 shows a schematic view of a first embodiment of a gas sensing device 1 for sensing a gas in a mixture of gases MG according to the disclosure.

The gas sensing device 1 comprises:

a photoacoustic spectrometry device 2, wherein the photoacoustic spectrometry device 2 comprises a radiator 3 configured for emitting light CL, wherein the photoacoustic spectrometry device 2 comprises a gas detection chamber 4 configured for exposing the mixture of gases MG to the light CL, wherein the photoacoustic spectrometry device 2 comprises a microphone 5 configured for detecting sound SO in the gas detection chamber 4, which is caused by exposing the mixture of gases MG to the light CL, and wherein the photoacoustic spectrometry device 1 is configured for generating signal samples SIG corresponding to a concentration of the gas in the mixture of gases MG based on the sound SO detected by the microphone 5; and a computing device 6 configured for receiving the signal samples SIG, wherein the computing device 6 comprises a feature extraction block 7 configured for calculating representations REP for the signal samples SIG so that for each of the signal samples SIG one of the representations REP is calculated, wherein each of the representations REP comprises one or more feature values FV, wherein each of the one or more feature values FV refer to a characteristic of the respective signal sample SIG, wherein the computing device 6 comprises a decision making block 8 which comprises a trained model based algorithm block 9 having a plurality of inputs 10 and at least one output 11, wherein the decision making block 8 comprises one or more trained models TM for the trained model based algorithm block 9, wherein each of the feature values FV of one of the representations REP is input to one of the inputs 10 of the trained model based algorithm block 9, so that each feature value FV of the feature values FV is fed into an individual input 10 of the inputs 10, wherein the decision making block 8 creates sensing results SR based on output values OV of the at least one output 11 of the trained model based algorithm block 9, wherein the output values OV are created by using at least one of the one or more trained models TM at the decision making block 8 so that the output values OV depend on the signal samples SIG of the photoacoustic spectrometry device 2.

In the example of FIG. 1 each of the representations REP consists of three feature values FV1, FV2 and FV3. The feature value FV1 is fed to the input 10.1, the feature value FV2 is fed to the input 10.2 and the feature value FV3 is fed to the input 10.3.

The output value OV, which is available at the sole output 11, is used as a sense result SR. In other embodiments the sense result SR is derived from the output value OV by post-processing block.

A further aspect of the disclosure relates to a method for operating a gas sensing device 1 for sensing a gas in a mixture of gases MG, wherein the gas sensing device 1 comprises a photoacoustic spectrometry device 2, wherein the photoacoustic spectrometry device 2 comprises a radiator 3 configured for emitting light CL, wherein the photoacoustic spectrometry device 2 comprises a gas detection chamber 4 configured for exposing the mixture of gases MG to the light CL, and wherein the photoacoustic spectrometry device 2 comprises a microphone 5 configured for detecting sound SO in the detection chamber 4, which is caused by exposing the mixture of gases MG to the light CL, and wherein the gas sensing device 1 comprises a computing device 6 comprising a feature extraction block 7 and a decision making block 8, wherein the decision making block 8 comprises a trained model based algorithm block 9 having a plurality of inputs 10 and at least one output 11, wherein the decision making block 8 comprises one or more trained models TM for the trained model based algorithm block 9, wherein the method comprises the steps of:

using the photoacoustic spectrometry device 2 for generating signal samples SIG corresponding to a concentration of the gas in the mixture of gases MG based on the sound SO detected by the microphone 5;

using the computing device 6 for receiving the signal samples SIG;

using the feature extraction block 7 for calculating representations REP for the signal samples SIG so that for each of the signal samples SIG one of the representations REP is calculated, wherein each of the representations REP comprises one or more feature values FV, wherein each of the one or more feature values FV refer to a characteristic of the respective signal sample SIG;

inputting each of the feature values FV of one of the representations REP to one of the inputs 10 of the trained model based algorithm block 9, so that each feature value FV of the feature values FV is fed into an individual input 10 of the inputs 11; and using the decision making block 8 for creating sensing results SR based on output values OV of the at least one output 11 of the trained model based algorithm block 8, wherein the output values OV are created by using at least one of the one or more trained models TM at the decision making block 8 so that the output values OV depend on the signal samples SIG of the photoacoustic spectrometry device 2.

Figure 2:
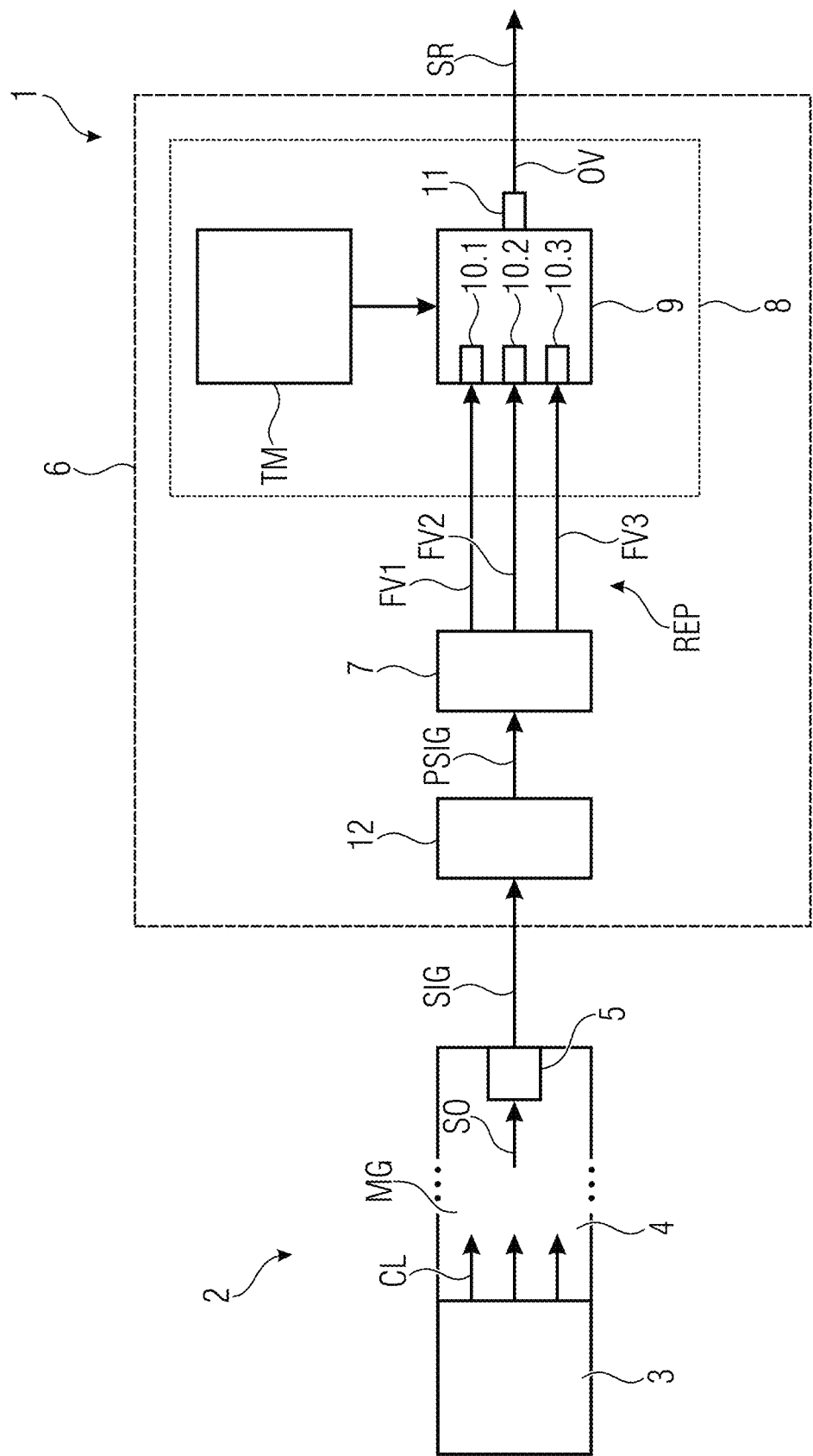
FIG. 2 shows a schematic view of a second embodiment of a gas sensing device according to the disclosure.

FIG. 2 shows a schematic view of a second embodiment of a gas sensing device 1 according to the disclosure. The second embodiment is based on the first embodiment. In the following only the additional features are explained.

According to embodiments of the disclosure the computing device 6 comprises a preprocessing block 12, wherein the preprocessing block 12 is configured for receiving the signal samples SIG from the photoacoustic spectrometry device 2, wherein the preprocessing block 12 is configured for generating a preprocessed signal sample PSIG for each of the signal samples SIG, and wherein the preprocessing block 12 is configured for forwarding the preprocessed signal samples PSIG to the feature extraction block 7.

In such embodiments each of the signal samples SIG is converted into a preprocessed signal sample PSIG by the preprocessing block 12. Each of the preprocessed signal samples PSIG is fed to the feature extraction block 7, which extracts the feature values FV1, FV2 and FV3, which refer to a characteristic of the respective signal sample SIG.

Figure 3:
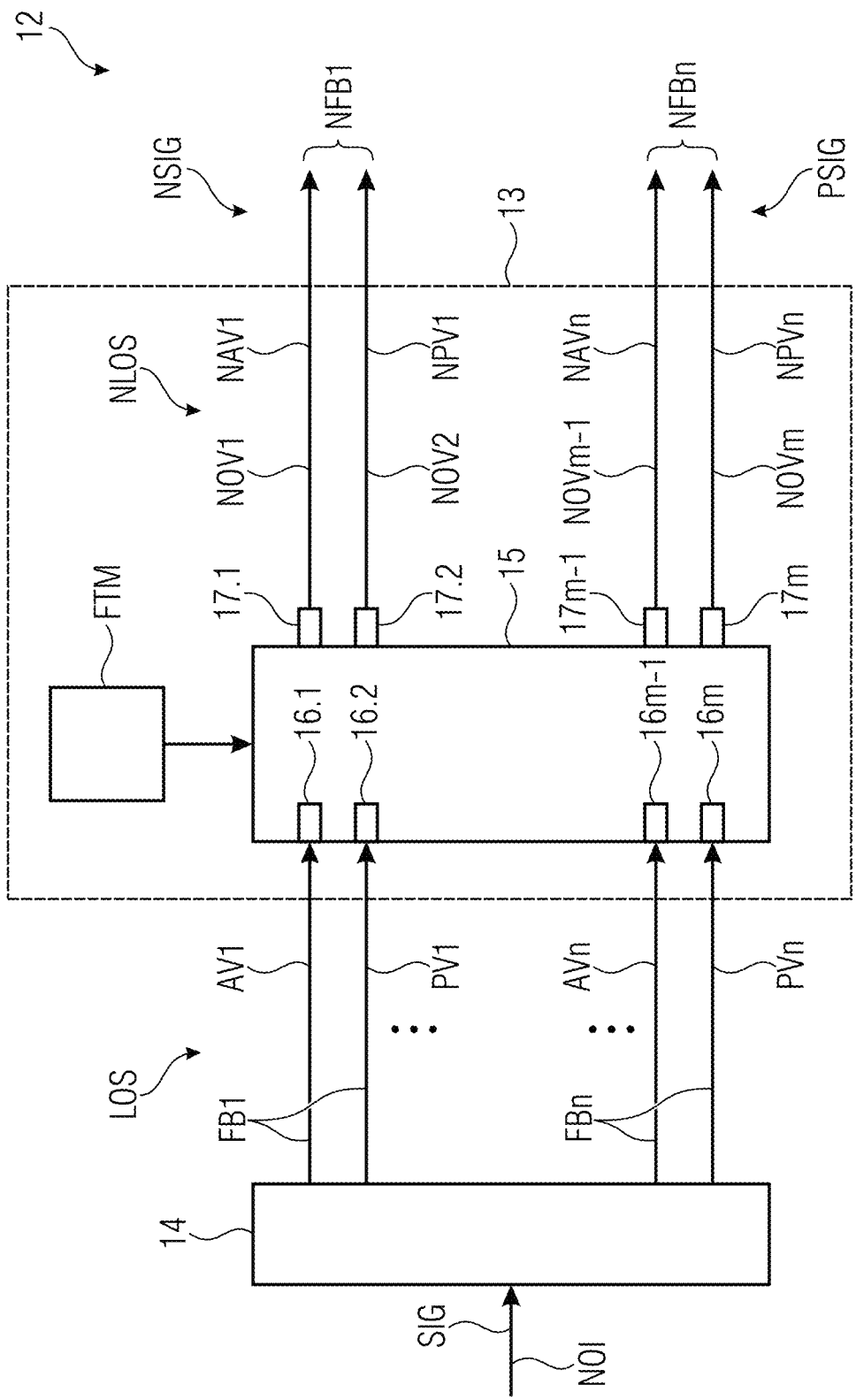
FIG. 3 shows a schematic view of a first preprocessing block for a gas sensing device according to the disclosure.

FIG. 3 shows a schematic view of a first preprocessing block 12 for a gas sensing device 1 according to the disclosure.

According to embodiments of the disclosure the preprocessing block 12 comprises a noise suppression block 13 configured for suppressing noise NOI in the signal samples SIG, so that the preprocessed signal samples PSIG comprise noise reduced signal samples NSIG having less noise NOI than the corresponding signal sample SIG.

According to embodiments of the disclosure the preprocessing block comprises a domain transform block 14 configured for transforming the signal samples SIG into a log-frequency domain, so as to obtain a logarithmic spectrum LOS having a plurality of frequency bands FB for each of the signal samples SIG, wherein the noise suppression block 13 comprises a further trained model based algorithm block 15 having a plurality of inputs 16 and a plurality of outputs 17, wherein the noise suppression block 13 comprises one or more further trained models FTM for the further trained model based algorithm block 15, wherein for each frequency band FB of the logarithmic spectra LOS of one of the signal samples SIG an amplitude value AV and a phase value PV are input to one of the inputs 16 of the further algorithm block 15, so that each of the amplitude values AV and each of the phase values PV are fed into an individual input of the inputs 16, wherein the noise suppression block 13 creates the noise reduced signal samples NSIG based on output values NOV of the outputs 17 of the further trained model based algorithm block 15, wherein the output values NOV of the further trained model based algorithm block 15 are created by using at least one of the one or more further trained models FTM at the noise suppression block 15, and wherein each of the output values NOV of the further trained model based algorithm block 15 is an noise reduced amplitude value NAV or a noise reduced phase value NPV of a noise reduced frequency band NFB of a noise reduced logarithmic spectra NLOS of one of the preprocessed signal samples PSIG.

The logarithmic spectrum LOS of each of the signal samples SIG, which comprise noise NOI, comprises n frequency bands FB1 to FBn. For a better overview only the frequency bands FB1 and FBn are shown. The frequency band FB1 comprises the amplitude value AV1 and the phase value PV1 and a frequency band FBn comprises the amplitude value AVn and the phase value PVn.

The further trained model based algorithm block 15 comprises m inputs 16 and m outputs 17. The amplitude value AV1 is fed to the input 16.1, the phase value PV1 is fed to the input 16.2, the amplitude value AVn is fed to the input 16$m$-1 and the phase value AVn is fed to the input 16$m$.

The noise reduced output value NOV1 of the output 17.1 is a noise reduced amplitude value NAV1 of the noise reduced frequency band NFB1 and the noise reduced output value NOV2 of the output 17.2 is a noise reduced phase value NPV1 of the noise reduced frequency band NFB1. The noise reduced output value NOVm-1 of the output 17$m$-1 is a noise reduced amplitude value NAVn of the noise reduced frequency band NFBn and the noise reduced output value NOVm of the output 17.$m$ is a noise reduced phase value NPVn of the noise reduced frequency band NFBn. the values NAV1, NPV1, NAVn and NPVn are part of the noise reduced logarithmic spectrum NLOS which is the noise reduced signal sample NSIG.

Figure 4:
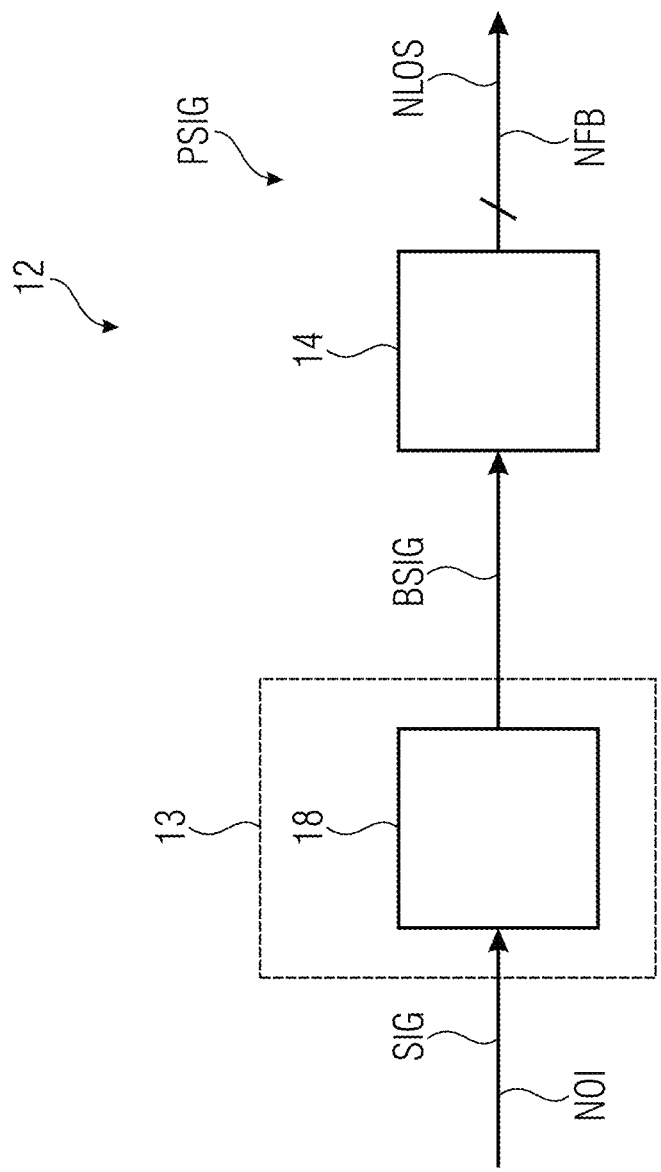
FIG. 4 shows a schematic view of a second preprocessing block for a gas sensing device according to the disclosure.

FIG. 4 shows a schematic view of a second preprocessing block 12 for a gas sensing devices according to the disclosure.

According to embodiments of the disclosure the preprocessing block 12 comprises a domain transform block 14 configured for calculating a logarithmic spectrum LOS having a plurality of frequency bands FB for each of the signal samples SIG.

According to embodiments of the disclosure the noise suppression block 13 comprises a band-pass filter 18 or a low-pass filter 18, so that the preprocessed signal samples PSIG are based on bandwidth reduced signal samples BSIG having a lower bandwidth than the corresponding signal sample SIG.

In the example of FIG. 4 each of the signal samples SIG is filtered by a band-pass filter 18 or a low-pass filter 18 in order to create a bandwidth reduced signal sample BSIG, which is transformed by the domain transform block 14 into the noise reduced logarithmic spectrum NLOS which is the noise reduced signal sample NSIG. In other embodiments the position of the blocks 14 and 14 could be exchanged.

Figure 5:
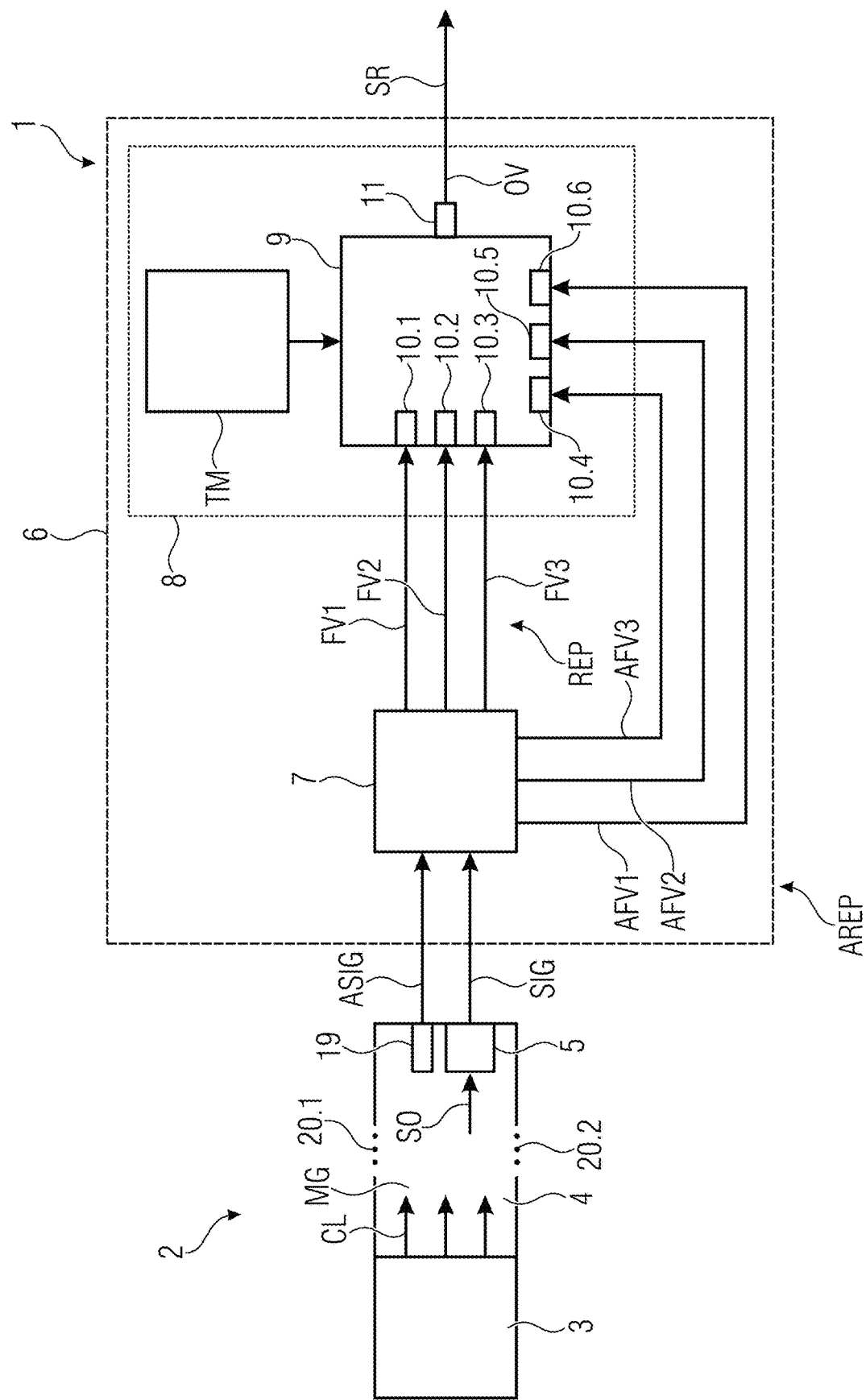
FIG. 5 shows a schematic view of a third embodiment of a gas sensing device according to the disclosure.

FIG. 5 shows a schematic view of a third embodiment of a gas sensing device 1 according to the disclosure. The third embodiment is based on the first embodiment. In the following only the additional features are explained.

According to embodiments of the disclosure the gas sensing device 1 comprises one or more auxiliary sensors 19, wherein each of the auxiliary sensors 19 is configured for generating auxiliary signal samples ASIG corresponding to a physical quantity of the mixture of gases MG;

wherein the one or more auxiliary sensors 19 comprise a temperature sensor 19 for generating first auxiliary signal samples ASIG of the auxiliary signal samples ASIG, which correspond to a temperature of the mixture of gases MG, and/or a pressure sensor 19 for generating second auxiliary signal samples ASIG of the auxiliary signal samples ASIG, which correspond to a pressure of the mixture of gases MG, and/or a humidity sensor 19 for generating third auxiliary signal samples ASIG of the auxiliary signal samples ASIG, which correspond to a humidity of the mixture of gases MG.

According to embodiments of the disclosure the decision making block 8 is configured for selecting one or more selected trained models TM from the one or more trained models TM based on the auxiliary signal samples ASIG of the one or more auxiliary sensors 19, wherein the output values OV of the at least one output of the trained model based algorithm block 9 are created by using the one or more selected trained models TM.

According to embodiments of the disclosure the decision making block 8 is configured for selecting the one or more selected trained models TM based on spectral information of the signal samples SIG.

According to embodiments of the disclosure the feature extraction block 7 is configured for calculating auxiliary representations AREP for the auxiliary signal samples ASIG so that for each of the auxiliary signal samples ASIG one of the auxiliary representations AREP is calculated, wherein each of the auxiliary representations AREP comprises one or more auxiliary feature values AFV, wherein each of the one or more auxiliary feature values AFV refer to a characteristic of the respective auxiliary signal sample ASIG; and wherein each of the auxiliary feature values AFV of one of the auxiliary representations AREP is input to one of the inputs 10 of the trained model based algorithm block 8, which is not used for inputting feature values FW, so that each of the auxiliary feature values AFV is fed into an individual input 10 of the inputs 10, wherein the output values OV of the trained model based algorithm block 8 are created so that the output values OV depend on the auxiliary signal samples ASIG.

According to embodiments of the disclosure the trained model based algorithm block 8 comprises a neural network using the one or more trained models TM and/or a random decision forest using the one or more trained models TM.

According to embodiments of the disclosure the detection chamber 4 comprises one or more ventilation openings 20 which are permanently open during an operational phase of the gas sensing device 1.

In the example of FIG. 5 an auxiliary sensor 19, which could be a temperature sensor 19, a pressure sensor 19 or a humidity sensor 19, is used for producing auxiliary signal samples ASIG, which are fed to the feature extraction block 7. The feature extraction block 7 establishes for each of the auxiliary signal samples ASIG an auxiliary representation AREP, wherein each of the auxiliary representations AREP comprises auxiliary feature values AFV1, AFV2 and AFV3. The auxiliary feature value AFV1 is fed to the input 10.4 of the trained model based algorithm block 9, the auxiliary feature value AFV2 is fed to the input 10.5 of the trained model based algorithm block 9 and the auxiliary feature value AFV3 is fed to the input 10.6 of the trained model based algorithm block 9. Thus, the output value OV of output 11, which is sensing results SR, depends on the feature values FV1, FV2, FV3 and on the auxiliary feature values AFV1, AFV2, AFV3.

The gas detection chamber 4 comprises to ventilation openings 20.1 and 20.2. It's obvious that the gas detection chamber for quick comprise more or less the intimidation openings.

Figure 6:
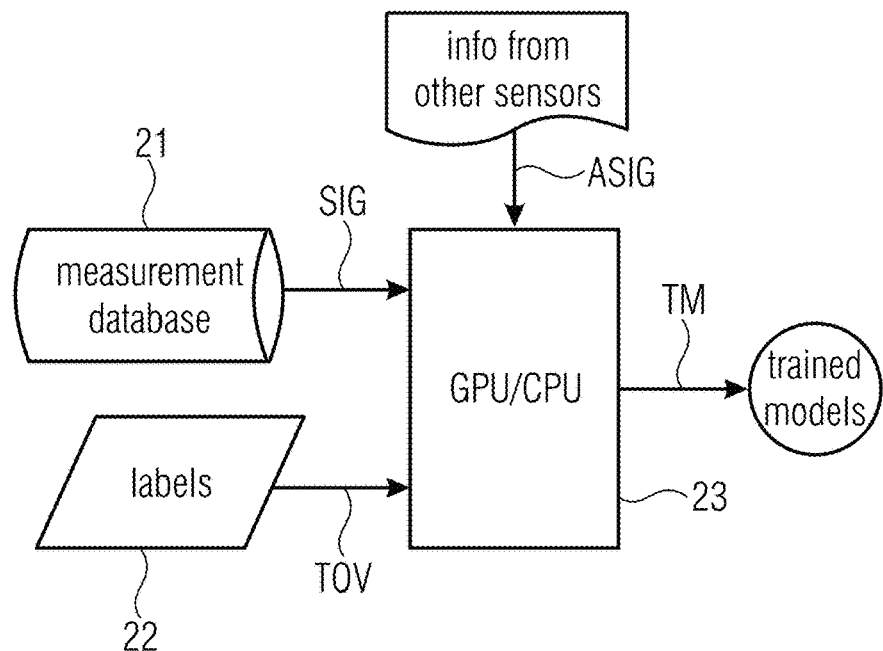
FIG. 6 illustrates a general approach of training a trained model for a gas sensing device according to the disclosure.

FIG. 6 illustrates a general approach of training a trained model TM for a gas sensing device 1 according to the disclosure.

In the training phase illustrated in FIG. 6, signal samples SIG stored in a measurement database 21 and target output values TOV stored in a label database 22 are given to a processing unit 23, for example a GPU or CPU, to optimize parameters of some chosen trained models TM. The 'other info' input corresponds to the auxiliary signal samples ASIG of other environmental sensors (such as a temperature, pressure or humidity) which enables the selection of a selected trained model TM out of a pool of trained models TM. Alternatively, the 'other info' inputs can be used as additional features to the same model. It is important that the measurement database 21 used for training covers the desired gas concentration range, different relevant noise realizations and different environmental conditions.

Figure 7:
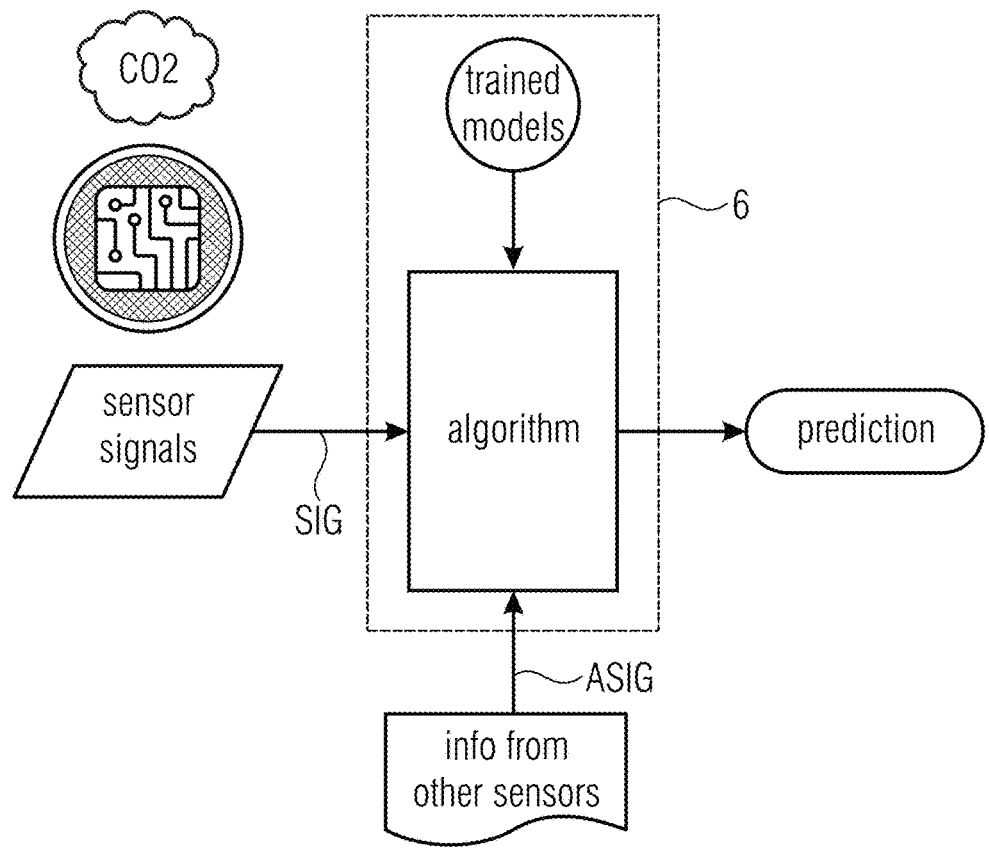
FIG. 7 illustrates a general approach of operating a gas sensing device according to the disclosure.

FIG. 7 illustrates a general approach of operating a gas sensing device 1 according to the disclosure.

The trained models TM established according to FIG. 6 are stored in the computing device 6, as shown in FIG. 7, to predict the gas concentration based on signal samples SIG from the photoacoustic spectrometry device 2 and based on the auxiliary signal samples ASIG from auxiliary sensors 19 in real time. Multiple trained models TM can be made available and then depending on the specific application or environmental condition the most appropriate trained model TM can be selected during the operational phase.

Figure 8:
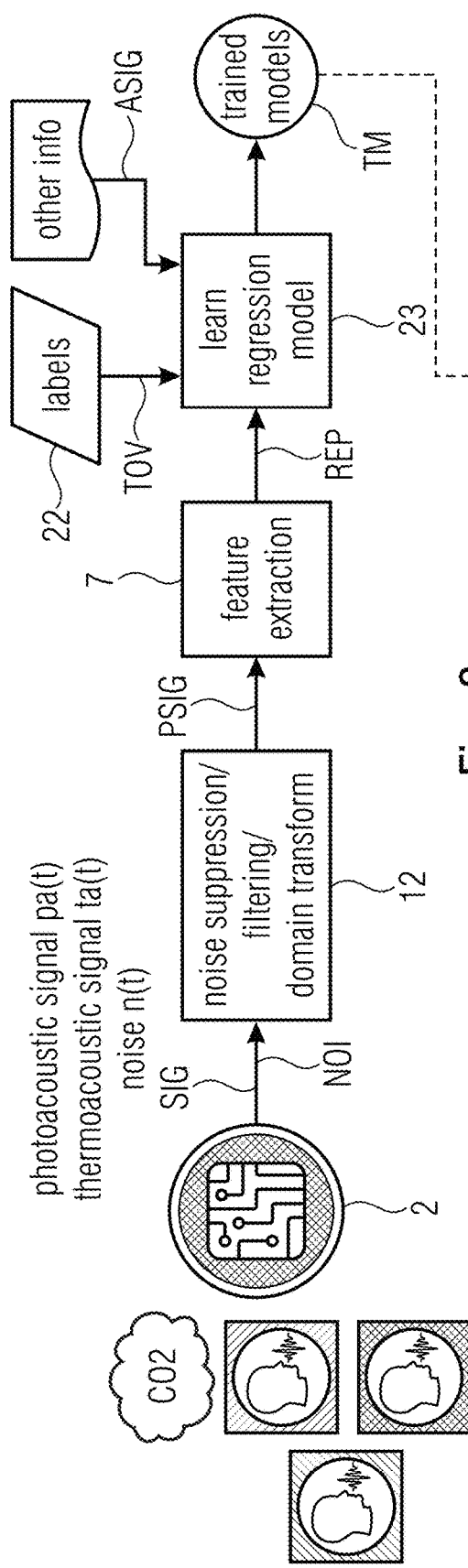
FIG. 8 illustrates a more specific approach of training a trained model for a trained model based algorithm block for a gas sensing device according to the disclosure.

FIG. 8 illustrates a more specific approach for training a trained model TM for a trained model based algorithm block 9 for a gas sensing device 1 according to the disclosure.

The incoming signal samples SIG n the training phase—sum of a photoacoustic signal as a function of time pa(t), a thermo-acoustic signal as a function of time ta(t) and noise NOI as a function of time n(t)—is first pre-processed at preprocessing block 12, in particular de-noised or filtered depending on the selected embodiment, converted to the log-frequency domain at preprocessing block 12 to simplify the handling of noises NOI with different spectral properties and fed as preprocessed signal samples PSIG to the feature extraction block 7 which creates the representations REP. Now, a trained model TM can be generated by the processing unit based on the representations REP, the target output values TOV and the auxiliary signal samples ASIG.

Figure 9:
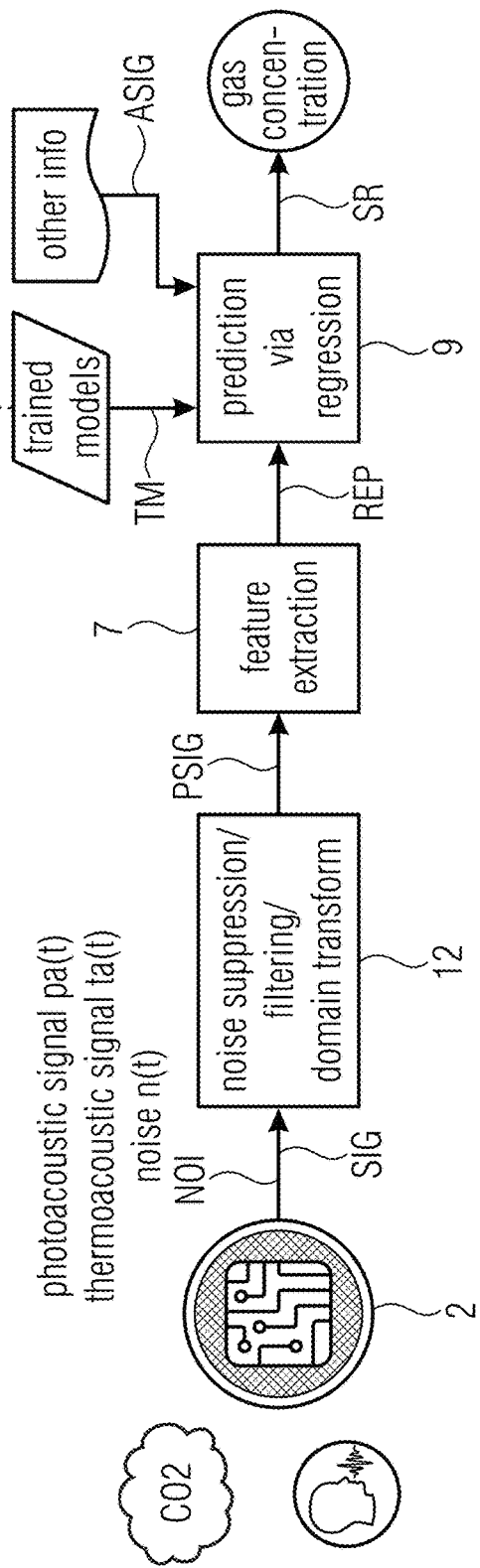
FIG. 9 illustrates a more specific approach of operating a gas sensing device according to the disclosure.

FIG. 9 illustrates a more specific approach of operating a gas sensing device 1 according to the disclosure.

The incoming signal samples SIG in the operational phase—sum of a photoacoustic signal as a function of time pa(t), a thermo-acoustic signal as a function of time ta(t) and noise NOI as a function of time n(t)—is first pre-processed at preprocessing block 12, in particular de-noised or filtered depending on the selected embodiment, converted to the log-frequency domain at preprocessing block 12 to simplify the handling of noises NOI with different spectral properties and fed as preprocessed signal samples PSIG to the feature extraction block 7 which creates the representations REP. Now, a gas prediction SR can be computed by the trained model based algorithm block 9 making use of the trained model TM, the representations REP and the auxiliary signal samples ASIG.

The trained model based algorithm block 9 can be implemented as a neural network 9 with a limited number of nodes i.e., neurons and hidden layers.

FIG. 10 illustrates a general approach for training a further trained model TM for a further trained model based algorithm block 15 for a noise suppression block 13 for a gas sensing device 1 according to the disclosure.

In some embodiments the noise suppression block 13 comprises a further trained model based algorithm block 15 and further trained models FTM which need to be trained separately from the trained models TM for the trained model based algorithm block 9. The further trained models FTM are established by a further processing unit 24 which makes use of the output SIG of the microphone 5 with and without noise as labels. This is the preferred choice for closed photoacoustic spectrometry devices 2 comprising valves or the like for controlling a gas flow into or out of the gas detection chamber 4 or for scenarios with better SNRs where nice performance can be achieved with limited complexity of the noise suppression stage which is conveniently implemented as a de-noising auto-encoder (lower SNRs normally implies a larger number of stages in the de-noising auto-encoder).

FIG. 11 illustrates a general approach of operating a first preprocessing block 12 for a gas sensing device 1 according to the disclosure.

The preprocessing block 12 comprises a domain transform block 14 and a noise suppression block 13 which comprises a further trained model based algorithm block 15 and further trained models FTM which are established as illustrated in FIG. 10.

Figure 12:
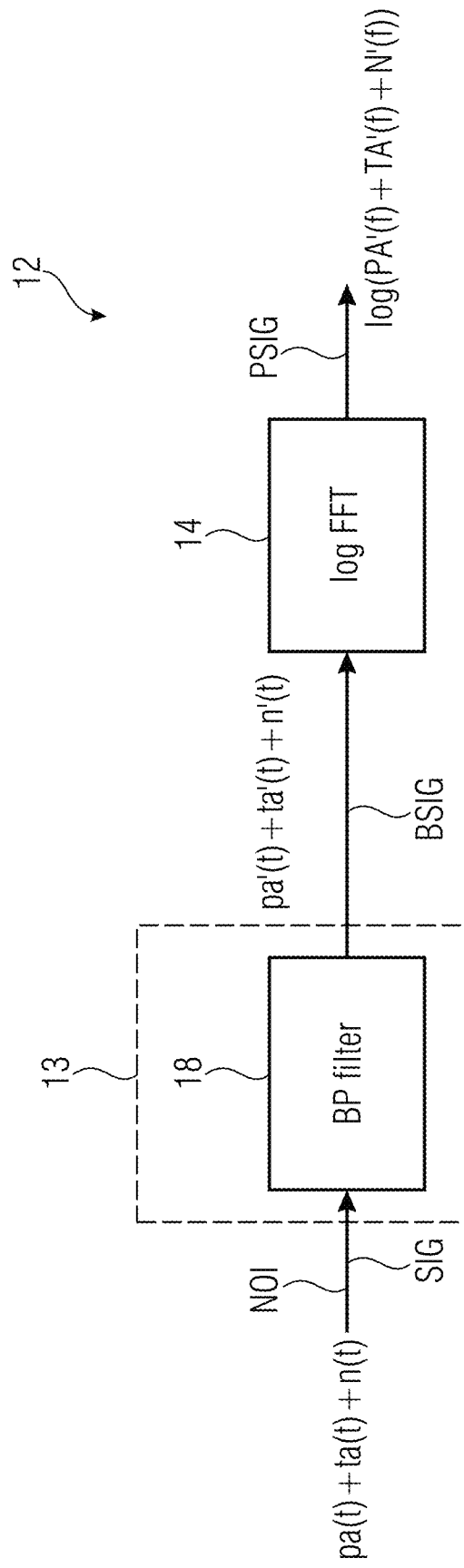
FIG. 12 illustrates a general approach of operating a second preprocessing block for a gas sensing device according to the disclosure.

FIG. 12 illustrates a general approach of operating a second preprocessing block 12 for a gas sensing device 1 according to the disclosure.

The preprocessing block 12 comprises a domain transform block 14 and a noise suppression block 13 which comprises a band-pass or low-pass filter 18. A part of the noise suppression task may be implemented by the trained model based algorithm block 9 together with the gas concentration estimation. This is the preferred choice if the designer has no access to the noiseless output of the microphone 5 or if two separate training phases (one for the noise suppression and one for the prediction of the gas concentration) are not desired for complexity reasons.

Figure 13:
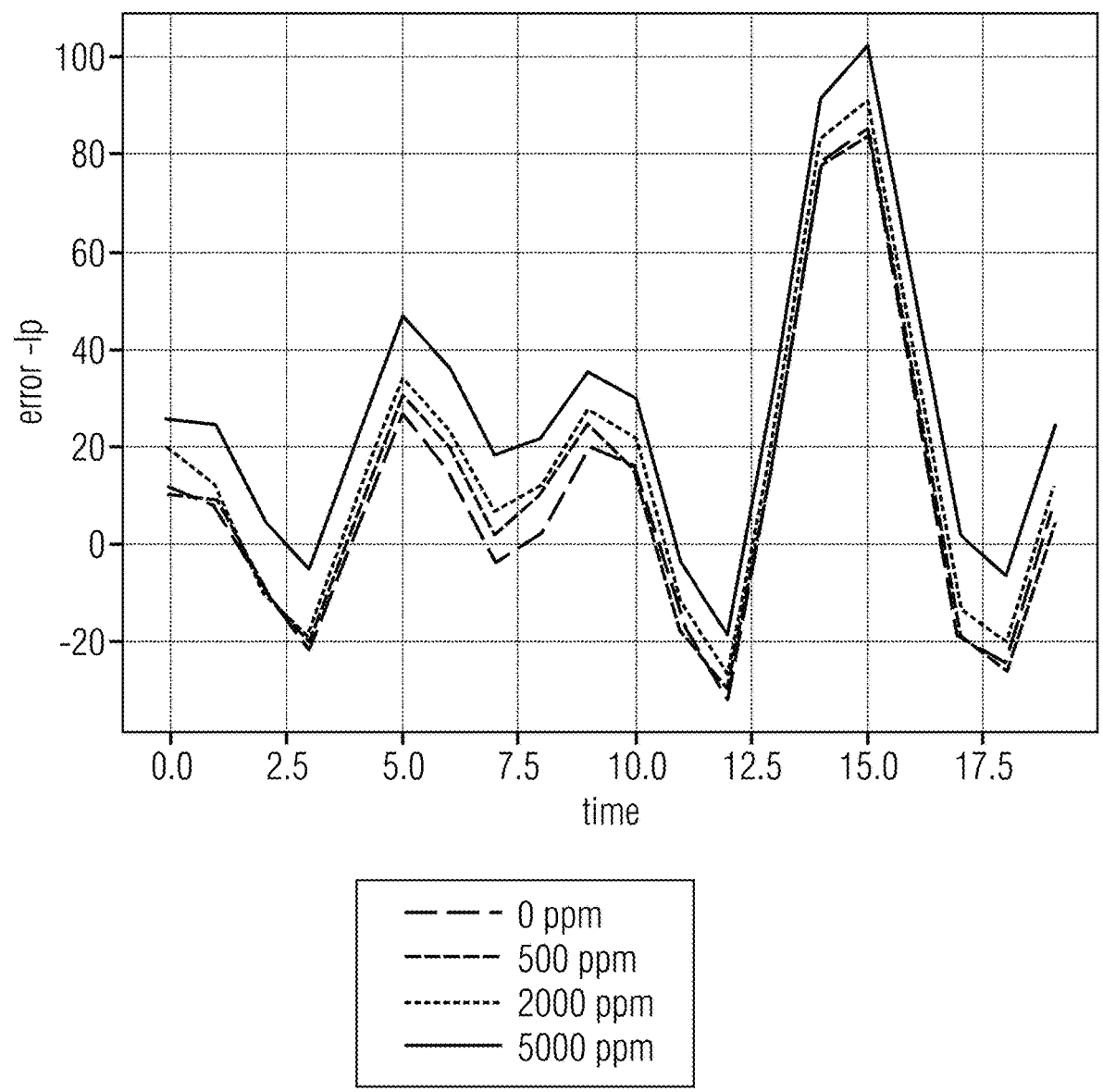
FIG. 13 illustrates an error generated by the presence of recorded speech at a gas sensing device according to prior art.

FIG. 13 illustrates an error generated by the presence of recorded speech at a gas sensing device 1 according to prior art.

Shown is an exemplary performance of a prior art device without noise suppression, with standard metric calibration and with a linear calibration algorithm. Illustrates here is the error generated by speech recordings.

Figure 14:
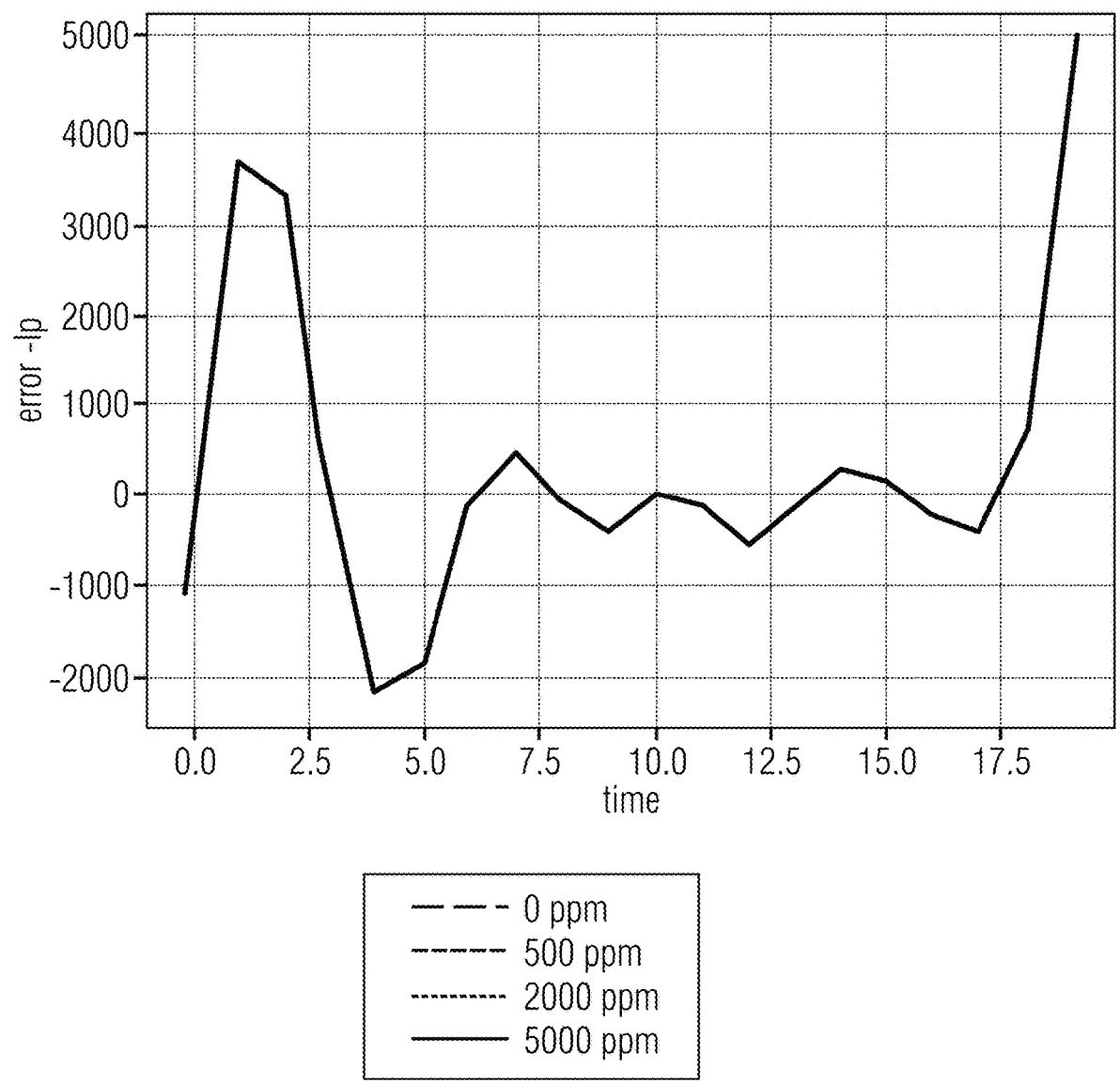
FIG. 14 illustrates an error generated by the presence of recorded music of Richard Strauss at a gas sensing device according to prior art.

FIG. 14 illustrates an error generated by the presence of recorded music of Richard Strauss at a gas sensing device 1 according to prior art.

Illustrated here is the error generated by music recordings with higher power in the low frequencies range. Errors of up to 5000 ppm are observed.

Figure 15:
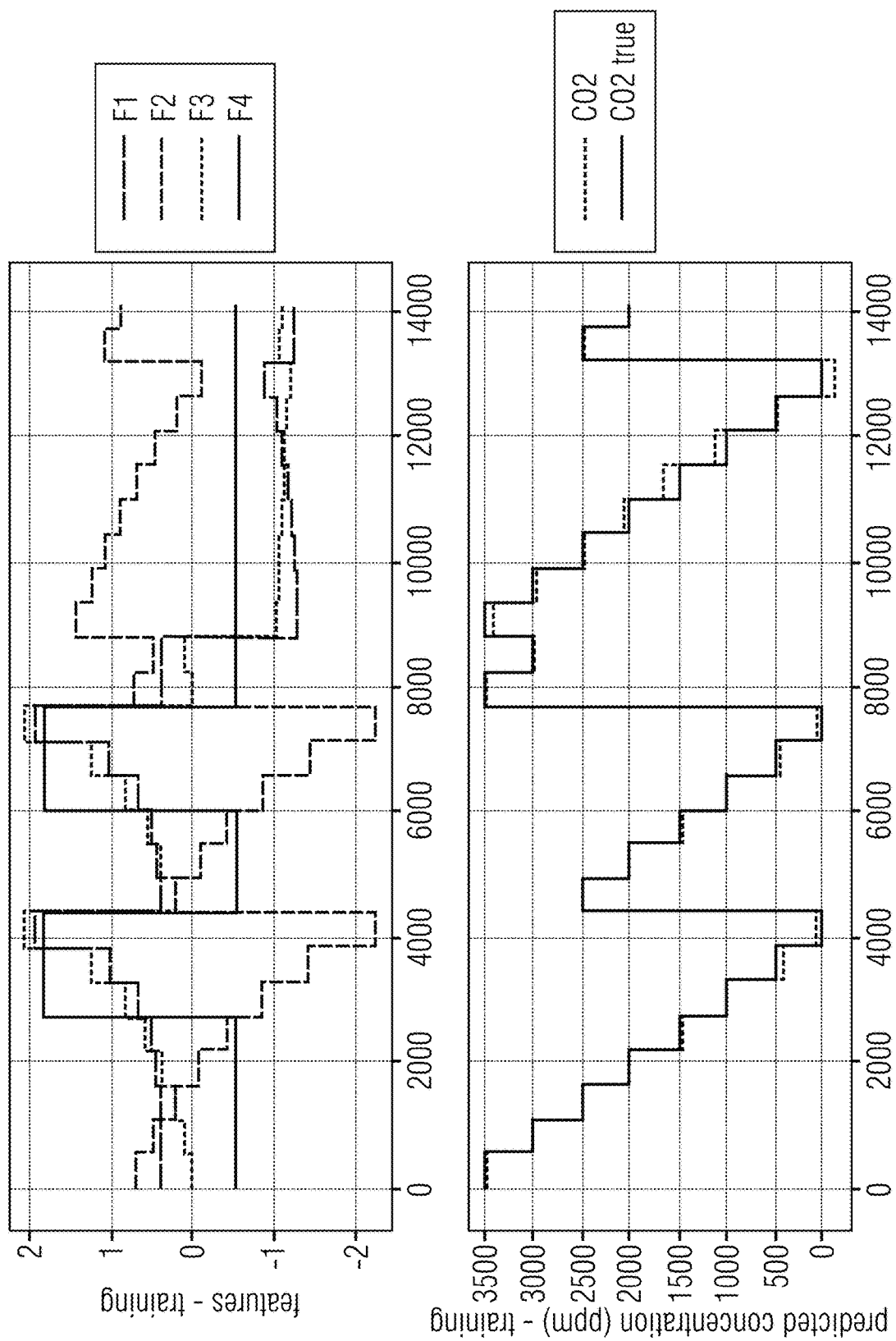
FIG. 15 illustrates a training phase for calculating a trained model.

FIG. 15 illustrates a training phase for calculating a trained model TM.

Figure 16:
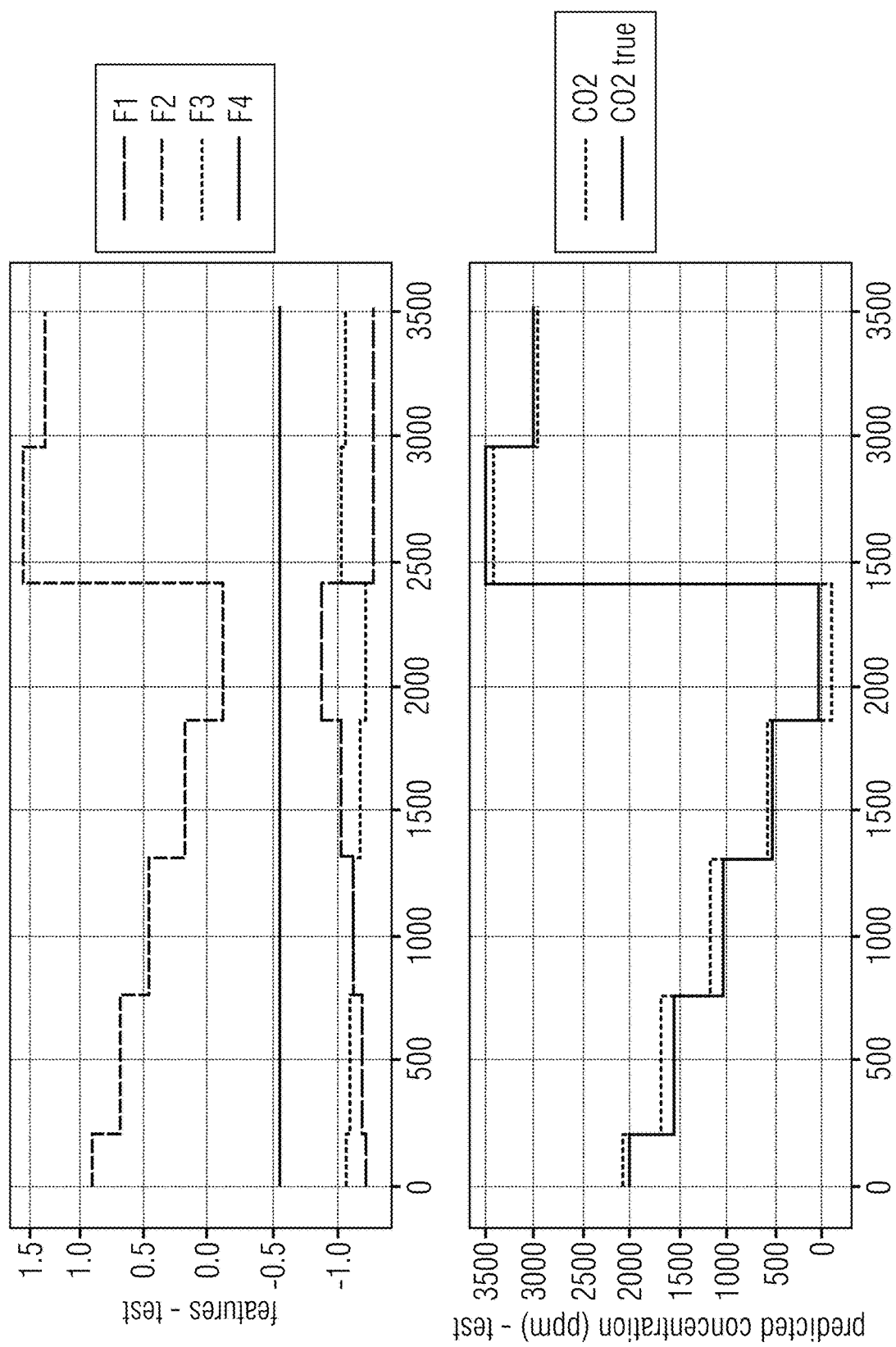
FIG. 16 illustrates an operating phase of a gas sensing device according to the disclosure.

FIG. 16 illustrates an operating phase of a gas sensing device 1 according to the disclosure.

Shown is the performance of the proposed device for different noise realizations (voice and Strauss music). While the original open photoacoustic spectrometry device 2 stays unchanged, a machine-learning based approach is used to suppress the acoustic noise. Simply modifying the processing chain leads to an average error of less than 100 ppm is obtained.

In case of closed photoacoustic spectrometry device 2, even better performance is expected when a noise suppression algorithm is introduced.

Elements of the disclosure are:

A noise suppression mechanism for photoacoustic gas sensors operating in the presence of different noise realizations. The mechanism overcomes current sensor limitations without hardware changes in the sensing element.

A related mechanism for gas concentration estimation which may map selected measured values (and their processed version) into a ppm output.

By judiciously exposing models to various noise and environmental conditions in the training phase conditions, a robust and compact prediction model is obtained which is able to cope with the residual acoustic noise from the previous stage as well as varying sensing environmental conditions such as temperature or pressure variations.

The extracted model can be embedded on the device and applied during the inference processing to the real time measured sensor (microphone) output samples.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A gas sensing device for sensing a gas in a mixture of gases, the gas sensing device comprising:
    a photoacoustic spectrometry device, wherein the photoacoustic spectrometry device comprises a radiator configured for emitting light, wherein the photoacoustic spectrometry device comprises a gas detection chamber configured for exposing the mixture of gases to the light, wherein the photoacoustic spectrometry device comprises a microphone configured for detecting sound in the gas detection chamber, which is caused by exposing the mixture of gases to the light, and wherein the photoacoustic spectrometry device is configured for generating signal samples corresponding to a concentration of the gas in the mixture of gases based on the sound detected by the microphone; and
    a computing device configured for receiving the signal samples, wherein the computing device comprises a feature extraction block configured for calculating representations for the signal samples so that for each of the signal samples one of the representations is calculated, wherein each of the representations comprises one or more feature values, wherein each of the one or more feature values refer to a characteristic of a respective signal sample,
    wherein the computing device comprises a decision making block which comprises a trained model based algorithm block having a plurality of inputs and at least one output, wherein the decision making block comprises one or more trained models for the trained model based algorithm block, wherein each of the feature values of one of the representations is input to one of the inputs of the trained model based algorithm block, so that each feature value of the feature values is fed into an individual input of the inputs, wherein the decision making block creates sensing results based on output values of the at least one output of the trained model based algorithm block, wherein the output values are created by using at least one of the one or more trained models at the decision making block so that the output values depend on the signal samples of the photoacoustic spectrometry device.

2. The gas sensing device according to claim 1, wherein the trained model based algorithm block comprises a neural network using the one or more trained models and/or a random decision forest using the one or more trained models.

3. The gas sensing device according to claim 1, wherein the computing device comprises a preprocessing block, wherein the preprocessing block is configured for receiving the signal samples from the photoacoustic spectrometry device, wherein the preprocessing block is configured for generating a preprocessed signal sample for each of the signal samples, and wherein the preprocessing block is configured for forwarding the preprocessed signal samples to the feature extraction block.

4. The gas sensing device according to claim 3, wherein the preprocessing block comprises a noise suppression block configured for suppressing noise in the signal samples, so that the preprocessed signal samples comprise noise reduced signal samples having less noise than the corresponding signal sample.

5. The gas sensing device according to claim 4, wherein the preprocessing block comprises a domain transform block configured for transforming the signal samples into a log-frequency domain, so as to obtain a logarithmic spectrum having a plurality of frequency bands for each of the signal samples,
    wherein the noise suppression block comprises a further trained model based algorithm block having a plurality of inputs and a plurality of outputs,
    wherein the noise suppression block comprises one or more further trained models for the further trained model based algorithm block, wherein for each frequency band of a logarithmic spectra of one of the signal samples an amplitude value and a phase value are input to one of the inputs of the further algorithm block, so that each of the amplitude values and each of the phase values are fed into an individual input of the inputs,
    wherein the noise suppression block creates the noise reduced signal samples based on output values of the outputs of the further trained model based algorithm block,
    wherein the output values of the further trained model based algorithm block are created by using at least one of the one or more further trained models at the noise suppression block, and
    wherein each of the output values of the further trained model based algorithm block is a noise reduced amplitude value or a noise reduced phase value of a noise reduced frequency band of a noise reduced logarithmic spectra of one of the preprocessed signal samples.

6. The gas sensing device according to claim 3, wherein the preprocessing block comprises a domain transform block configured for calculating a logarithmic spectrum having a plurality of frequency bands for each of the signal samples.

7. The gas sensing device according to claim 4, wherein the noise suppression block comprises a band-pass filter or a low-pass filter, so that the preprocessed signal samples are based on bandwidth reduced signal samples having a lower bandwidth than the corresponding signal sample.

8. The gas sensing device according to claim 1, wherein the gas sensing device comprises one or more auxiliary sensors, wherein each of the auxiliary sensors is configured for generating auxiliary signal samples corresponding to a physical quantity of the mixture of gases;
wherein the one or more auxiliary sensors comprise
a temperature sensor for generating first auxiliary signal samples of the auxiliary signal samples, which correspond to a temperature of the mixture of gases, and/or
a pressure sensor for generating second auxiliary signal samples of the auxiliary signal samples, which correspond to a pressure of the mixture of gases, and/or
a humidity sensor for generating third auxiliary signal samples of the auxiliary signal samples, which correspond to a humidity of the mixture of gases.

9. The gas sensing device according to claim 8, wherein the decision making block is configured for selecting one or more selected trained models from the one or more trained models based on the auxiliary signal samples of the one or more auxiliary sensors, wherein the output values of the at least one output of the trained model based algorithm block are created by using the one or more selected trained models.

10. The gas sensing device according to claim 1, wherein the decision making block is configured for selecting the one or more selected trained models based on spectral information of the signal samples.

11. The gas sensing device according to claim 8, wherein the feature extraction block is configured for calculating auxiliary representations for the auxiliary signal samples so that for each of the auxiliary signal samples one of the auxiliary representations is calculated, wherein each of the auxiliary representations comprises one or more auxiliary feature values, wherein each of the one or more auxiliary feature values refer to a characteristic of the respective auxiliary signal sample; and
wherein each of the auxiliary feature values of one of the auxiliary representations is input to one of the inputs of the trained model based algorithm block, which is not used for inputting feature values, so that each of the auxiliary feature values is fed into an individual input of the inputs, wherein the output values of the trained model based algorithm block are created so that the output values depend on the auxiliary signal samples.

12. The gas sensing device according to claim 1, wherein the detection chamber comprises one or more ventilation openings which are permanently open during an operational phase of the gas sensing device.

13. A method for operating a gas sensing device for sensing a gas in a mixture of gases, wherein the gas sensing device comprises a photoacoustic spectrometry device, wherein the photoacoustic spectrometry device comprises a radiator configured for emitting light, wherein the photoacoustic spectrometry device comprises a gas detection chamber configured for exposing the mixture of gases to the light, and wherein the photoacoustic spectrometry device comprises a microphone configured for detecting sound in the detection chamber, which is caused by exposing the mixture of gases to the light, and wherein the gas sensing device comprises a computing device comprising a feature extraction block and a decision making block, wherein the decision making block comprises a trained model based algorithm block having a plurality of inputs and at least one output, wherein the decision making block comprises one or more trained models for the trained model based algorithm block, wherein the method comprises:
using the photoacoustic spectrometry device for generating signal samples corresponding to a concentration of the gas in the mixture of gases based on the sound detected by the microphone;
using the computing device for receiving the signal samples;
using the feature extraction block for calculating representations for the signal samples so that for each of the signal samples one of the representations is calculated, wherein each of the representations comprises one or more feature values, wherein each of the one or more feature values refer to a characteristic of a respective signal sample;
inputting each of the feature values of one of the representations to one of the inputs of the trained model based algorithm block, so that each feature value of the feature values is fed into an individual input of the inputs; and
using the decision making block for creating sensing results based on output values of the at least one output of the trained model based algorithm block, wherein the output values are created by using at least one of the one or more trained models at the decision making block so that the output values depend on the signal samples of the photoacoustic spectrometry device.

\* \* \* \* \*